US005646002A

United States Patent [19]
Linsley et al.

[11] Patent Number: 5,646,002
[45] Date of Patent: Jul. 8, 1997

[54] METHOD FOR INCREASING THE SENSITIVITY OF ASSAYS FOR TARGET LIGAND

[75] Inventors: Peter S. Linsley; Vincent Ochs; Diane Horn; Joseph P. Brown, all of Seattle, Wash.

[73] Assignee: Oncogen Limited Partnership, Seattle, Wash.

[21] Appl. No.: 195,987

[22] Filed: Feb. 14, 1994

Related U.S. Application Data

[63] Continuation of Ser. No. 703,587, May 20, 1991, abandoned, which is a continuation of Ser. No. 107,040, Oct. 9, 1987, abandoned.

[51] Int. Cl.[6] .................................................. G01N 33/53
[52] U.S. Cl. ........................ 435/7.23; 435/7.1; 435/18; 436/64; 436/813; 436/543; 436/825
[58] Field of Search ............................. 530/395; 435/7.1, 435/18, 68.1, 172.2, 240.27, 810, 292, 7.23; 436/813, 63, 64, 543, 825

[56] References Cited

U.S. PATENT DOCUMENTS

| | | | |
|---|---|---|---|
| 4,116,776 | 9/1978 | Dalbow et al. | |
| 4,146,603 | 3/1979 | Davidson et al. | 424/1 |
| 4,708,930 | 11/1987 | Kortright et al. | 435/7 |
| 4,743,543 | 5/1988 | Kortright | 435/7 |
| 4,762,800 | 8/1988 | Rettig et al. | 436/548 |
| 4,853,326 | 8/1989 | Quash et al. | 435/7 |

FOREIGN PATENT DOCUMENTS

| | | |
|---|---|---|
| 88118727 | 11/1988 | European Pat. Off. |
| 8701392 | 3/1987 | WIPO |

OTHER PUBLICATIONS

Lan et al, Cancer Research, vol. 45, pp. 305–310 Jan. 1985.
Linsley et al.(1986, Oct.) Cancer Research 46: 5444–5450.
Linsley et al.(1986, Dec.) Cancer Research 46: 6380–6386.
Gallo et al., "The Cerebrospinal Fluid Transferrin/Tau Proteins" *J. Neurol. Sciences* 70:81–92 (1985).
Feizi et al., "Mucin–Type Glycoproteins", *Biochem. Soc. Transact.* 12:591–596 (1984).
(Abstr.) "Determination of human chorionic gonadotropin by enzyme immunoassay" (Abstr. No. 98:101922f) *Chem. Abstr.* 98:146 Toyo Jozo Co., Ltd. (1983).
(Abstr.) "Structural analysis of the O–glycosidically linked core–region oligosaccharides of human meconium glycoproteins which express oncofetal antigens" *Chem. Abstr.* (Abstr. #102:183507n) 102:448 by Hounsell et al. (1985).
(Abstr.) "Altered biologic and immunologic activities of progressively desialyated human urinary FSH" *Chem. Abstr.* 75:17 (1971) (Abstr. #126325b) by Vaitukaitis et al.
Koprowski et al., *Science*, 212:53–55 (1981), "Specific Antigen in Serum of Patients with Colon Carcinoma".
Holmgren et al., *Br. Med. J.* 288:1479–82 (1984), "Detection by Monoclonal Antibody of Carbohydrate Antigen CA 50 in Serum of Patients with Carcinoma".

Metzgar et al., *PNAS* 81:5242–5246 (1984), "Detection of A Pancreatic Cancer–Associated Antigen (DU–PAN–2 Antigen) in Serum and Ascites of Patients with Adenocarcinoma".
Kannagi et al., *Cancer Res.* 46:2619–2626 (1986), "Quantitative and Qualitative Characterization of Human Cancer–associated Serum Glycoprotein Antigens Expressing Fucosyl or Sialyl–Fucosyl Type 2 Chain".
Johnson et al., *Cancer Res.* 46:850–857 (1986) "Analysis of a Human Tumor–Associated Glycoprotein (TAG–72) Identified by Monoclonal Antibody B72.3".
Macartney, J., *J. Pathol.* 150:135–144 (1986), "Lectin Histochemistry of Galatose and N–Acetyl–Galactosamine Glycoconjugates in Normal Gastric Mucosa and Gastric Cancer and the Relationship with ABO and Secretor Status".
Feizi et al., *Biochem. Soc. Trans.* 12:591–599 (1984), "Tumour–associated and Differentiation Antigens on the Carbohydrate Moieties of Mucin–Type Glycoproteins".
Brown et al., *Clin. Chem.*, 27:1592–1596 (1981), "Use of Monoclonal Antibodies for Quantitative Analysis of Antigens in Normal and Neoplastic Tissues".
Linsley et al., *Cancer Res.*, 46:5444–5450 (1986), "Elevated Levels of a High Molecular Weight Antigen Detected by Antibdy W1 in Sera from Breast Cancer Patients".
Linsley et al., *Cancer Res.*, 46:6380–6386 (1986), "Heritable Variation in Expression of Multiple Tumor Associated Epitopes on a High Molecular Weight Mucin–like Antigen".
Kohler and Milstein, *Nature* 256:495 (1975), "Continuous Cultures of Fused Cells Secreting Antibody of Predefined Specificity".
Frankel et al., *J. Biol. Response Modifiers*, 4:273–286 (1985), "Tissue Distribution of Breast Cancer–Associated Antigens Defined by Monoclonal Antibodies".
Fenderson et al., *Mol. Immunol.*, 23:747–754 (1986), "A Monoclonal Antibody Defining a Binary N–Acetyllactosaminyl Structure in Lactoisooctaosylceramide (IV$^6$Galβ1→4GlcNAcnLc$_6$) : A Useful Probe for Determining Differential Glycosylation Patterns Between Normal and Transformed Human Fibroblasts".
Hellstrom, *Cancer Research*, 46:3917–3923 (1986), "Monoclonal Mouse Antibodies Raised Against Human Lung Carcinoma".
Young et al., *J. Biol. Chem.* 256:10967–10972 (1981), "Two Monoclonal Anticarbohydrate Antibodies Directed to Glycosphingolipids with a Lacto–N–glycosyl Type II Chain".
Creeth et al., *Biochem. J.* 167:557–569 (1977), "The Separation and Characterization of Bronchial Glycoproteins by Density–Gradient Methods".
Dion et al., *Biotechniques*, (Sep. 1983), "Glycopeptide Detection by Covalent Attachment to Microplate Wells and Lectin Binding".

Primary Examiner—Toni R. Scheiner
Attorney, Agent, or Firm—Townsend and Townsend and Crew LLP

[57] ABSTRACT

A method for treating serum samples to remove sialic acid from ligands to expose binding sites to enhance immunological binding, for use in assays and to generate novel anti-ligands is described. The method includes treatment of serum using neuraminidase.

10 Claims, 4 Drawing Sheets

METHOD FOR INCREASING THE SENSITIVITY OF ASSAYS FOR TARGET LIGAND

This a continuation of application Ser. No. 07/703,587, filed May 20, 1991, now abandoned, which is a continuation of Ser. No. 07/107,040, filed Oct. 9, 1987, now abandoned.

FIELD OF THE INVENTION

This invention relates to a process for treating ligands to enhance immunological binding.

BACKGROUND OF THE INVENTION

Assays have been developed for detecting and quantifying the presence of substances of interest using immunological binding. Such assays include those which use antibodies which recognize a region or "epitope" on an antigenic molecule, responsible for the specific interaction of the antigen with the antibody. Of particular interest are assays capable of detecting substances in a fluid sample such as blood serum, for example, certain glycoproteins and glycolipids which have been found to be associated with tumor tissues and may thus serve as tumor markers. Recently, a class of high molecular weight glycoproteins known as mucins, containing large amounts of carbohydrates, has been found to be tumor-associated. Monoclonal antibodies capable of detecting epitopes on mucin antigens have been described. Immunoassays using such monoclonal antibodies have shown promise for the detection and monitoring of cancer in humans. These antibodies reactive with mucins include CA 19–9, (Koprowski et al., Science, 212:53–54 (1981)); CA 50, (Holmgren et al., Br. Med. J. 280:1479–82 (1984)); DUPAN-2, (Metzgar et al., PNAS 81:5242–5246 (1984)); and antibody to sialylated Le$^x$ epitope (Kannagi et al., Cancer Res. 46:2619–2626 (1986)).

Sialic acids, which are O-acyl derivative of N-acetyl neuraminic acid, an amino sugar acid, are widely distributed in human tissues as constituents of lipids, polysaccharides and of mucoproteins. Sialic acid occurs in various forms which differ in their acyl side chains. Sialic acids containing O-acetyl, O-methyl and O-glycolyl constituents have been described.

Tumor cells have been found to contain relatively large amounts of sialic acid, and mucin antigens present in serum derived from cancer patients have been reported to be sialylated. The enzyme neuraminidase removes sialic acid. In some cases, it has been observed that the ability of a monoclonal antibody to bind with an epitope on a mucin antigen normally recognized by the antibody is decreased after digestion of the antigen using neuraminidase. (Kannagi et al., supra). It has also been observed that neuraminidase treatment can render tumor associated glycoproteins more immunologically reactive (U.S. Pat. No. 4,146,603). Based on these observations, neuraminidase sensitivity has been used to assist in the characterization of epitopes recognized by various antibodies.

The resulting decrease in the ability of "neuraminidase sensitive" antibodies to bind to neuraminidase treated sialylated antigen has been explained by suggesting that sialic acid is required for proper three-dimensional conformation of these binding sites. (Johnson et al., Cancer Res., 46:850–857 (1986)). Other sialylated tumor-associated antigens include the Lewis blood group antigens and carcinoembryonic antigen (CEA) (Kannagi et al., supra).

Because sialic acid is generally found as a terminal residue in oligosaccharide side chains, it may also block or "mask" epitopes. For example, lectin binding sites in gastric tumors are exposed following removal of sialic acid using neuraminidase (Macartney, J. Pathol. 150:135–144 (1986)). In addition to sialic acid, other peripheral sugars such as fucose also interfere with immunological binding sites on ligands such as antigens. The removal of such peripheral substances may reveal "core" carbohydrates in proteins (Feize et al., Biochem. Soc. Trans. 12:591–599 (1984)) which contain binding sites not otherwise exposed. These core structures are common in oligosaccharide chains from many sources, and, in general, do not exhibit the restricted tissue distribution of peripheral oligosaccharide structures such as the Lewis blood group antigens.

Previous methods for removing peripheral sugars from proteins have required purification of ligand prior to treatment. It would thus be beneficial to develop a method for removing substances from ligands such as antigens without prior purification to make additional immunological binding sites available to serve as improved disease or infection markers.

SUMMARY OF THE INVENTION

The present invention provides a method for treating unpurified ligands to remove from the ligands substances such as sialic acid which may interfere with immunological binding to the ligand. The method uses enzymatic digestion or exposure to mild acid to remove the interfering substances to expose additional binding sites. Neuraminidase is a preferred enzyme for treatment of the ligand.

The treated ligand may be used in immunological assays to detect binding of anti-ligand to ligand, where labeled anti-ligand is contacted with the treated ligand, and the bound anti-ligand is detected. The treated ligand may also be used as an immunogen to generate hybridomas to produce monoclonal antibodies. Such antibodies may be useful in assays to detect ligands, including mucin antigens, associated with disease or infection in a mammalian subject.

BRIEF DESCRIPTION OF THE DRAWING

The details of typical embodiments of the present invention will be described in connection with accompanying drawings in which.

DETAILED DESCRIPTION OF THE INVENTION

Figure 1:
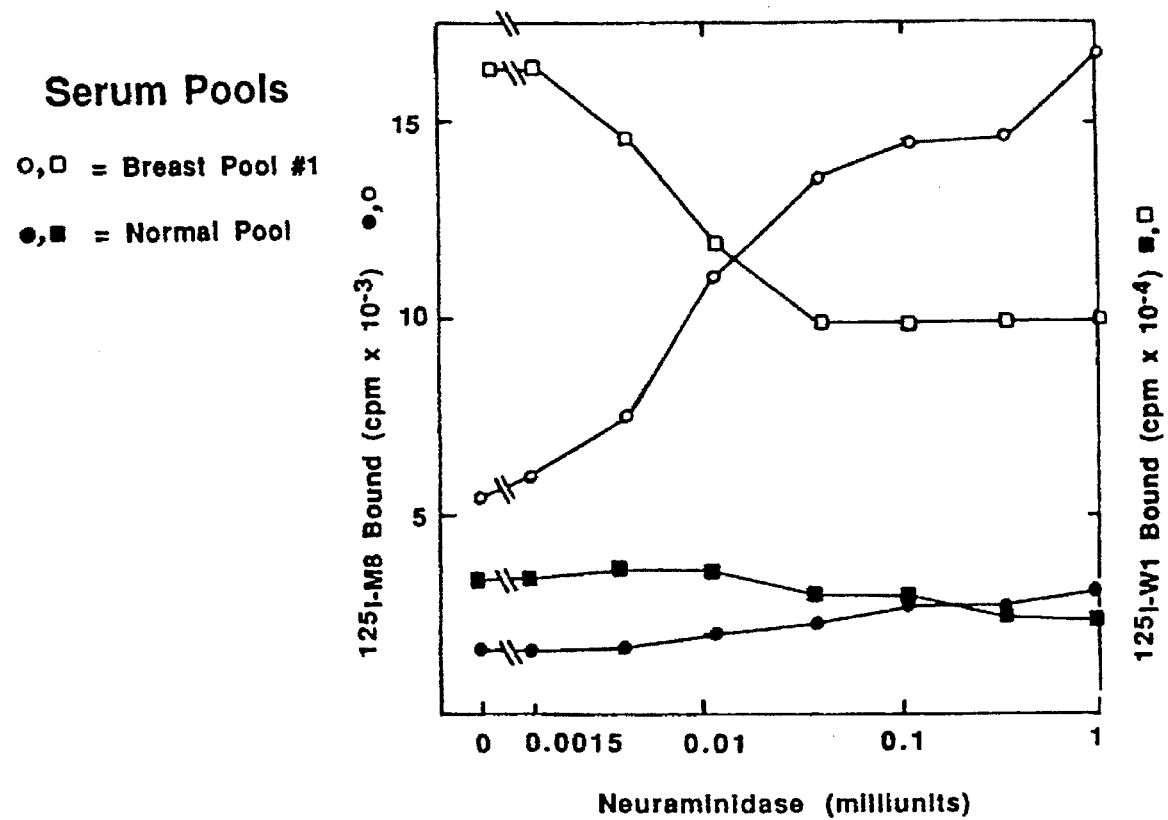
FIG. 1 depicts the binding of the ONC-M8 and W1 antibodies to antigen present in pooled serum from normal human subjects, as compared to binding of the antibodies to antigen present in pooled serum from humans with breast cancer, as a function of increasing neuraminidase concentration.

We have found that immunological binding to a ligand may be enhanced by treating ligand using enzymatic digestion to remove substances and expose binding sites on the ligand. These results suggest that sialic acid may be inactivating or otherwise making certain binding sites or "epitopes" unavailable for immunological binding.

The present invention describes a method for increasing immunological binding to certain ligands, particularly where the ligand is present in unpurified form at low concentration in complex mixtures of proteins and glycoproteins such as human blood serum. As used herein "ligand" means a target substance, with reactive binding sites that participate in immunological binding with an "anti-ligand" that recognizes the binding site or sites on the ligand. Antigen and antibody are well-known examples of ligand and anti-ligand. According to the method, target ligand is treated to remove substances which interfere with immunological binding, and thus expose additional binding sites. For example, mucin antigen may be treated with an enzyme, such as neuraminidase, which removes sialic acid. This treatment results in enhanced binding of certain antibodies to the mucin antigen, which, in turn, results in more sensitive assays capable of detecting low concentrations of ligand even in complex protein mixtures such as whole blood serum. In addition this method may expose additional and novel binding sites ("epitopes") on antigen for use in screening antibodies or for generation of hybridomas to produce novel monoclonal antibodies.

The mechanism by which the present method of treatment of a ligand to remove substances from binding sites leads to enhanced binding of certain anti-ligands is not well understood. For some previously described mucin-directed antibodies, it was believed that the removal of substances such as sialic acid would decrease antibody recognition of an antigen, due to alteration of the structure of the binding site. However, while not wishing to be bound by this explanation, it may be that specific binding sites on ligands, such as tumor-associated mucin antigens, which are not expressed on ligands obtained from normal sources, form part of the core ligand structure which is exposed by removal of peripheral sugars, making these binding sites available for binding to anti-ligands such as antibodies. Alternatively, removal of sialic acid may alter overall conformation of the ligand molecule (Lan et al., *J. Cellular Biochem.*, Abst. 309, 110:160 (1987)). These binding sites may be new or rare, for example, epitopes which are preferentially expressed on antigens associated with disease or infection. Alternatively these sites may be "repeating"; i.e. multiple binding sites which are recognized by a single anti-ligand.

Since relatively few different core and backbone O-linked carbohydrate structures have been described, these structures may be common components of oligosaccharide chains from widely distributed tissue sources and may thus serve as general tissue markers. Therefore, removing peripheral sugars as described by the method of the invention may provide such core and backbone oligosaccharides for use as targets in immunological assays to detect various forms of disease and infection, including cancer.

Although the example describes the treatment of mucin antigen, particularly antigen derived from tumor sources, any ligand present in a body fluid may be treated to remove substances such as sialic acid to promote Carcino-Embryonic immunological binding. For example, non-mucin antigens such as Carcino-Embryonic Antigen (CEA), and Human Chorionic Gonadotropin (HCG), may be treated with neuraminidase, or using other procedures as described below. Using this method the ligand may be unpurified, e.g., present in body fluids such as whole blood serum, sputum, urine or may be provided in ascites of effusion fluid from cancer patients, and the fluid containing ligand directly treated and used in an assay. Alternatively, the ligand may be isolated and purified for treatment using known purification techniques or as described in co-pending U.S. patent application Ser. No. 932,781, filed Nov. 19, 1986, assigned to the same assignee as herein and incorporated by reference herein.

The treated ligand may be used to enhance the sensitivity of an immunoassay (i.e. the ability of the assay to detect the presence of the ligand at low concentrations). Such assays may provide the ability to detect the presence of ligand associated with disease or infection or may function as screening tests to evaluate binding of anti-ligand to treated ligand, for example to screen antibodies present in hybridoma supernatants, or in samples from various sources.

The preferred enzyme for treating mucin antigen present in whole blood serum is neuraminidase enzyme, for example, neuraminidase isolated from *Vibrio cholerae* (available from CALBIOCHEM Brand Biochemicals, La Jolla, Calif.). Using this enzyme, digestion of ligand is preferably carried out using temperatures in the range of from 4° to 37° C. at an enzyme concentration of 0.1 to 6 milliUnits (mU)/microliter (µl) of serum diluted in a buffer of 0.15M NaCl, 50 mM sodium acetate, pH 5.5, 0.1% $CaCl_2$ and 0.1% $NaN_3$. Digestion is stopped after sufficient incubation by raising the pH to neutrality, or by briefly heating at temperatures in the range of 55° C. to 95° C.

The process of enzyme digestion is preferably monitored by measuring the effects of treatment in using an immunological assay. For example, a titration curve may be developed to determine the correct concentration of enzyme to be used by using increasing amounts of enzyme, up to 500 mU/µl and recording the resulting binding of anti-ligand to the target ligand. The preferred enzyme concentration is that at which the binding effects are maximal. An alternative method to monitor digestion determines the proportion of de-sialylated transferrin (a sialylated glycoprotein that is a major component of serum) present in a sample of serum containing the target ligand and that is being treated with neuraminidase, using sodium dodecyl sulfate polyacrylamide gel electrophoresis (SDS/PAGE).

In addition to enzymatic digestion, other chemical treatments may be used to remove blocking peripheral sugars from the core ligand structure, including using mild acid. For example, a sample of body fluid may be treated with acid such as sulfuric acid ($H_2SO_4$) using an effective amount of the acid to provide enhanced binding of anti-ligand to a ligand present in the sample. The appropriate amounts of acid may be pre-determined by testing for continued or enhanced reactivity of the glycoprotein or other ligand with anti-ligand after the acid treatment.

A ligand/anti-ligand immunoassay may be used to evaluate the results of treatment of a ligand as described herein, by determining the ability of the ligand to be detected by anti-ligand. The assay chosen to evaluate binding to the treated ligand may use one or two anti-ligands in a competitive or noncompetitive, direct or indirect format as is known in the art. As described above, the ligand is preferably provided in a fluid sample such as whole serum, without requiring isolation and purification steps. The ligand may also be provided in association with cells, for example cancer cells. The ligand in impure form in the fluid or cellular sample is treated, for example, with neuraminidase, as described above.

An immunoassay procedure may then be used in which a single anti-ligand, for example a monoclonal antibody, is bound to a solid phase, and the same monoclonal antibody is added to the fluid sample, but is labeled for use as a probe.

The labeled monoclonal antibody binds to the same binding site on the ligand recognized by the monoclonal antibody bound to the solid phase, but which is repeated on the ligand. Alternatively, the immunoassay can be performed using a combination of two anti-ligands each reactive with a distinct binding site on the subject ligand. Such an assay might provide even better specificity than an assay using either anti-ligand type alone. Radioimmunoassays, enzyme assays and fluorescent assays using one of the above assay formats are known. In these assays, at least one anti-ligand is labeled, for example, with a radionuclide, color-producing enzyme, or fluorophore, using well-know procedures. Anti-ligand labeled using standard procedures may then be contacted with the treated ligand, for example ligand digested with neuraminidase, and the effects on binding of the anti-ligand can be noted by detecting the label.

A particularly useful assay and the assay preferred for use in the method of this invention, is the "double determinant immunoassay" or "DDIA," a direct assay, described by Brown et al., *Clin Chem.*, 27:1592–1596 (1981) and Linsley et al., *Cancer Res.*, 46:5444–5450 (1986), both incorporated by reference herein. In that assay, a suitable substrate is coated with a solution of monoclonal antibody known to be reactive with a particular antigen. For example, using the method described herein, tumor-associated mucin antigen present in whole blood serum from a human patient suspected of having a disease such as cancer, is digested with neuraminidase enzyme, and reacted with immobilized antibody. A second antibody, which may be either the same or different from the immobilized antibody, is radiolabeled with Iodine-125 ($I^{125}$), and is then added to the substrate and the radioactivity of bound, labeled antibody is measured using an instrument for detecting radiation, such as a gamma counter. Alternatively, the antibody may be labeled with horseradish peroxidase (HRP), which may be detected using a spectrophotometer to measure the intensity of the color (yellow) which forms when the HRP reacts with its substrate, for example ortho-phenylenediamine (OPD).

Histological procedures may also be used to evaluate antibody binding to treated ligand using samples consisting of cells taken from a subject. Antibody binding may be determined using HRP-conjugated antibody and a fluorescent label on the antibody such as fluorescein isothiocyanate and by observing the resulting fluorescent pattern as described by Linsley et al. in *Cancer Res.* 46:6380–6386 (1986), incorporated by reference herein.

Immunoassays, as described above, may be used with ligand treated according to the method described herein, to provide a procedure for selecting anti-ligands capable of binding to the treated ligand, preferably ligand associated with the presence of disease or infection in mammalian subjects. For this application, ligand is treated as described herein to make previously unexposed binding sites available. The treated ligand may then be systematically exposed to a variety of anti-ligands, to detect anti-ligand capable of binding to the binding sites. Thus, previously known anti-ligands which have failed to react with untreated ligand, may be identified and rendered useful for detection of ligand, particularly ligand associated with disease or infection.

The method of the present invention may also be used to generate hybridomas which may produce novel monoclonal antibodies by using treated antigen as immunogen. Such antibodies may include those which preferentially react with binding sites expressed on the disease or infection associated form of the antigen. To prepare such hybridomas, the hybridization technique described by Kohler and Milstein, *Nature* 256:495 (1975) is used with modifications. A suitable host mammal, such as a mouse, is immunized with purified antigen, for example mucin antigen derived from a tumor source, as described in co-pending U.S. patent application Ser. No. 932,781. The antigen is treated prior to immunization, for example by digesting with neuraminidase enzyme. The mice are inoculated intraperitoneally with the purified, neuraminidase-treated antigen and are subsequently boosted using similar amounts of purified antigen, typically several days following the last immunizing injection. Spleens are collected from the immunized hosts a few days after the final boost, and spleen cells are isolated for fusion. An immortalizing cell line, such as a myeloma cell line, i.e., a cell line which can be maintained perpetually, for practical purposes, in cell culture, and which is capable of conferring its immortal properties on a non-transformed cell line when fused, may be used for fusion with the spleen cells. The immortalizing cells and spleen cells are then fused and the cells are separated from the fusion medium, and grown in a growth medium, such as HAT medium, to eliminate unhybridized parent cells. The resulting fused cells, or hybridomas, may be increased in number, and the hybridoma supernatants are then assayed for reactivity (i.e. "screened"), for example, with tumor-associated mucin antigen.

It is contemplated that using the procedures described above, antigens which, when previously treated with neuraminidase, yielded decreased binding with various antibodies, may be used as immunogen to attempt to generate antibodies to novel binding sites that become available for binding as a result of such treatment, and thus improve the recognition of these antigens which may be useful markers for diseased or infected tissues.

The foregoing assays, as well as histological procedures may also be used to ascertain the nature and extent of a disease or to monitor the progress of the disease by detecting the presence of disease-associated ligand. For example, to detect cancer, the amount of tumor-associated antigen detected using the present invention may be compared to the amount of antigen typically found in samples derived from normal tissues. An increase in the amount of antigen detected over time may signify an increase in tumor mass, while a decrease may indicate decreased tumor mass. To assess the stage of a disease, the amount of antigen detected will be compared to the amount found to be typical of various disease states. To monitor the progress of disease, samples such as serum, may be taken periodically (the length of the period will depend upon the patient history and treatment) and the amounts of antigen compared.

The method of the present invention may thus permit the development of improved, i.e. more sensitive and more specific, immunoassays for detecting the presence of disease or infection in humans. The assays may be improved as a result of the exposure of additional binding sites on treated ligand such as an antigen for binding to anti-ligands, for example, antibodies directed to core structure binding sites (epitopes) on an antigen. The availability of additional binding sites may permit lower levels of disease-associated ligand present in a serum sample to be detected in an immunological assay. Thus, diseases such as cancer may be detected and diagnosed in the earlier stages when less disease-associated ligand is being produced.

The use of novel monoclonal antibodies produced using treated antigen as immunogen, may also improve an assay which uses the antibodies to detect antigen, based on higher specificity of the antibodies for the treated antigen. If the epitopes exposed by treatment are rare, for example, present on the tumor-associated antigen but not on antigen derived from normal sources, an immunoassay to detect tumor-associated antigen using a sample treated with neuraminidase may be rendered more specific for the detection of the antigen. This is because the improved binding of antibody to the treated antigen may permit the assay to discriminate between the presence of tumor-associated antigen and normal antigen from patients without cancer. This reduces the occurrence of so called "false positive results" in assays, in which the presence of cancer is falsely indicated because the antibody may be binding to mucin antigen present in samples from normal patients.

In addition, the method set forth herein provides a convenient procedure for assaying a body fluid sample taken from a subject, because ligand in the sample may be directly treated without requiring tedious and time-consuming protein purification steps. The sample may thus be simultaneously treated to expose binding sites on the ligand and to assay for anti-ligand binding to the exposed sites.

The method of the present invention may be provided in the form of a diagnostic test kit for assaying a sample from a human subject for the presence of a particular ligand. Such a kit may contain monoclonal antibody or antibodies, such as that produced by hybridoma ATCC HB9209, reactive with epitopes on tumor mucin antigen, and an enzyme for treating ligand, for example neuraminidase enzyme. The enzyme may be provided as a component of the diluant used to dilute the sample containing ligand in the assay procedure. Preferably, the kit also includes instructions for carrying out the assay and for treating ligand according to the method of the invention.

The following examples are presented to illustrate the present invention and to assist one of ordinary skill in making and using the same. The examples are not intended in any way to otherwise limit the scope of the disclosure or the protection granted by Letters Patent granted hereon.

EXAMPLE I

Serum Assay for Mucin Antigen

Monoclonal Antibodies

Monoclonal antibodies, W1 and ONC-M8 which recognize the W1 and M8 epitopes, respectively, on mucin antigen, were used. The W1 antibody has been previously described (referred to as "2G3" by Frankel et al., *J. Biol. Response Modifiers*, 4:273–286 (1985)) and was obtained from Cetus Corporation, Emeryville, Calif. The ONC-M8 monoclonal antibody (American Type Culture Collection (ATCC) 12301 Parklawn Drive, Rockville, Md. 20852 on Sep. 24, 1986. Accession No. HB9209) is described in co-pending U.S. patent application, Ser. No. 932,781, filed Nov. 19, 1986, and assigned to the same assignee as the present invention, the disclosure of which is incorporated by reference herein, and was obtained from Oncogen, Seattle, Wash. Other antibodies which were tested were the C6 antibody which recognizes the "T" epitope (described by Fenderson et al., *Mol. Immunology*, 23:747–754 (1986), and was provided by Drs. Bruce Fenderson and S. Hakomori, Fred Hutchinson Cancer Research Center (FHCRC, Seattle, Wash.); the L17 antibody which recognizes the blood group epitope Lewis x (Le$^x$) (ATCC No. HB8739, Mar. 1, 1985 described by Hellstrom, *Cancer Research*, 46:3917–3923 (1986) and obtained from Dr. I. Hellstrom, Oncogen, Seattle, Wash.); and 1B2 antibody which recognizes the "i" epitope (described by Young et al., *J. Biol. Chem.* 256:10967–10972 (1981) and provided by Dr. Hakomori, FHCRC, Seattle, Wash.). Antibody 1B2 was used as ascites fluid. C6 was used in culture supernatant. Antibodies W1, ONC-M8 and L17 were purified from ascites fluid.

Sera

Blood serum was drawn from human patients and allowed to clot at 23° C. for 10 to 90 minutes. Samples were then stored at 4° to 6° C for 0.5 to 5 hours prior to centrifugation in a clinical centrifuge. Blood serum was separated from the clotted fraction, aliquoted and frozen at −70° C. For some tests, sera from patients was pooled. Pooled serum was obtained from 10 to 16 normal individuals and 8 to 17 advanced breast cancer patients.

Neuraminidase Treatment

Serum samples obtained from normal human subjects and from those diagnosed as having breast cancer as described above, were diluted in neuraminidase treatment buffer to a concentration of 20% (vol:vol). Fifty (50) µl of diluted serum was then mixed with 50 µl of neuraminidase enzyme diluted in neuraminidase buffer and the mixture was incubated at 37° C. for 16 hours. The serum-enzyme mixture was then diluted with an equal volume of 50 mM Tris, pH 8 containing 0.5% BSA to stop the reaction. The mixture was then further diluted to an optimum dilution for the DDIA assay described below using the W1 or ONC-M8 antibody (1:200 and 1:100 final concentration, respectively).

Detection of Treated Antigen in Serum

The application of the present process to treat mucin antigen present in whole blood serum was demonstrated with a DDIA using the W1 and ONC-M8 antibodies and sera from 16 cancer and 17 normal patients. The procedure used in the DDIA was as follows. The assay was performed on the sera prepared as described above, both on individual samples and on pooled serum. Immulon II (Dynatech Laboratories, Chantilly, Va.) plates were incubated with 50 µl /well of a solution of 10 µg/ml W1 antibody (0.5 µg antibody in a volume of 0.05 ml of 0.05M Tris buffer, pH 8.0) for one hour at 23° C. to coat the plates. The plates were then aspirated and blocked using 200 µl/well of blocking buffer (0.5% bovine serum albumin (BSA) and 5% sucrose in Tris, pH 8.0) for one hour to overnight at 23° C. The plates were again aspirated and towel blotted.

50 µl of diluted sera (1:200 for W1, 1:100 for ONC-M8), from tumor and normal patients, either pooled or individual samples, controls and standards were pipetted into the coated plates. The plates were sealed and incubated at room temperature for one hour. The plates were then manually rinsed twice using 2% FCS in phosphate buffered saline (PBS) buffer. Next, 50 µl of an appropriate dilution of W1-HRP or ONC-M8-HRP or W1-$^{125}$I or ONC-M8-$^{125}$I antibody conjugate was added to the plates. A concentration of 0.5 µg/ml of HRP or $^{125}$I antibody conjugates was used. The plates were resealed and incubated for one hour at room temperature. The plates were then manually rinsed three times using PBS. Binding of W1-HRP and ONC-M8-HRP conjugates was detected by adding a solution of OPD (100 µl ) (Zymed Laboratories, Inc., San Francisco, Calif.) at a concentration of 0.5 mg/ml in 100 mM sodium citrate at pH 5.0, containing 0.0075% (vol/vol) $H_2O_2$. A yellow color resulted from the reaction of substrate with enzyme. 100 µl of OPD substrate was reacted by incubation in the dark for one hour and stopped using 100 µl of 1.5N sulfuric acid ($H_2SO_4$). The enzyme substrate reaction was read in units of optical density (O.D.) at 490 nm using a microwell plate reader (Genetic Systems Corp., Seattle, Wash.). Binding of $^{125}$I-conjugates was detected using a gamma counter. Standards were also made for the W1 and ONC-M8 antibodies by volumetrically diluting effusion fluids containing mucin antigen. The standards were calibrated by assigning the pools of control sera a value of 20 units/ml. Standards and controls were aliquoted and stored at −70° C.

Results

As shown in FIG. 1, $^{125}$I-labeled ONC-M8 antibody exhibited an increased binding to neuraminidase-treated mucin antigen present in pooled tumor sera derived from breast cancer patients, as compared to binding of the ONC-M8 antibody in pooled sera from normal patients. On the other hand, 125I-labeled W1 antibody demonstrated a decreased ability to bind mucin antigen in sera pooled from breast cancer patients as compared to the ability of W1 antibody to bind to antigen in normal pooled sera with increasing neuraminidase concentration. The ONC-M8 antibody exhibited slightly increased binding to antigen in normal pooled serum with increasing neuraminidase concentration, as compared to the W1 antibody. However, the increase in binding to normal sera with ONC-M8 was less than the increase in binding of ONC-M8 to tumor sera after neuraminidase treatment. This indicates that detection of certain binding sites on mucin antigen such as ONC-M8 may be facilitated by treatment of whole blood serum with neuraminidase.

Figure 2:
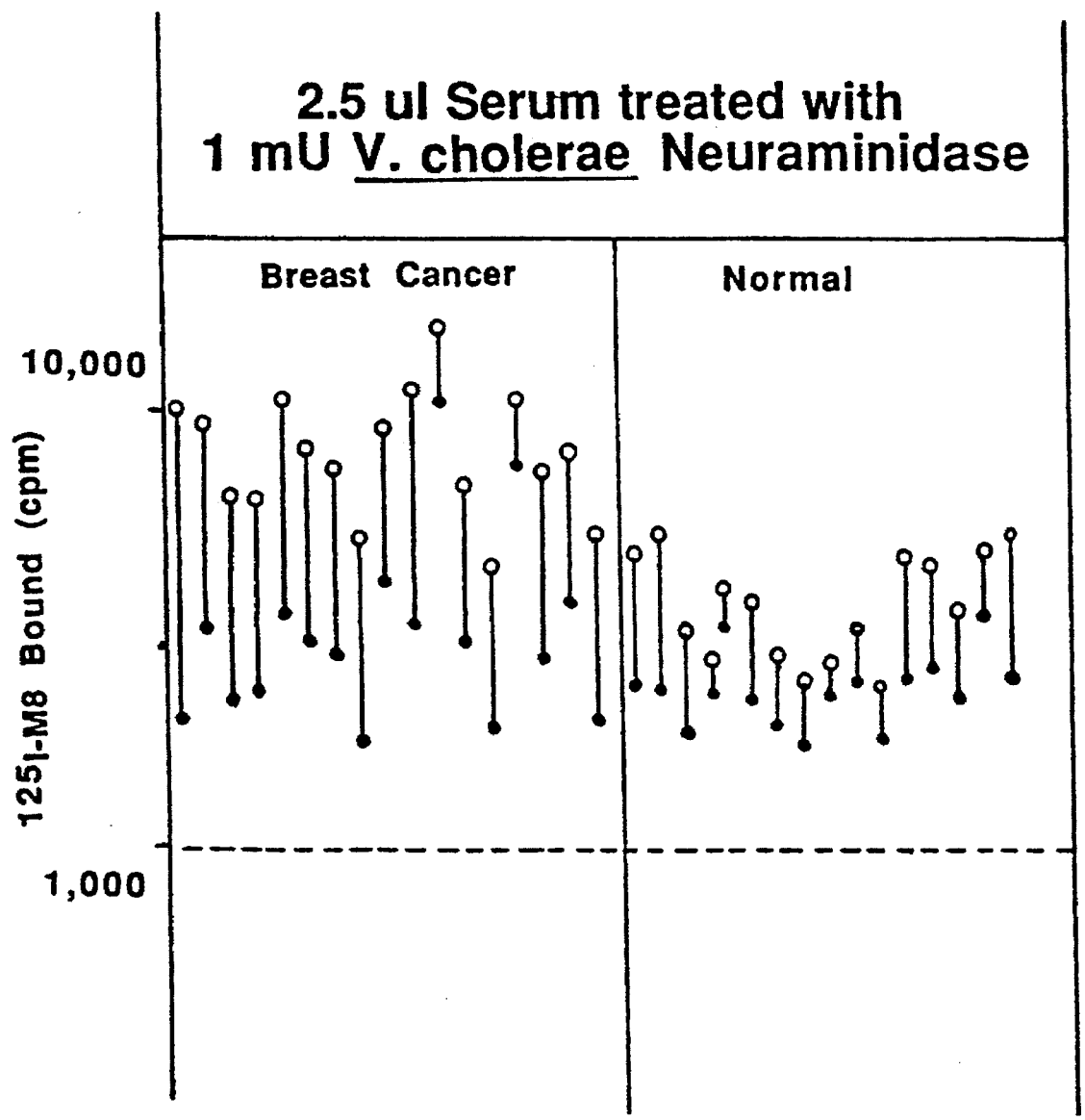
FIG. 2 is a chart of the binding of ONC-M8 antibody to antigen present in individual serum samples from normal human subjects and from humans with breast cancer, after treatment with neuraminidase.

When individual serum samples from the 17 normal human patients and those from patients with breast cancer (16 patients) were treated with 1 mU/neuraminidase the levels of antigen detected by $^{125}$I-labeled ONC-M8 antibody were observed to increase in all the breast cancer patients that made up the pooled sera results shown in FIG. 1. Binding to antigen in the individual samples from the normal humans was also increased (FIG. 2).

These results suggest that in a serum assay, the presence of tumor-associated antigen may be detected by certain antibodies (i.e. as "positive" results in the assay) in a greater percent of subjects when the serum samples have been treated with neuraminidase.

EXAMPLE II

Antibody Binding to Purified Antigen Treated With Neuraminidase

Purified Mucins

Mucins were purified from normal human milk and pleural effusion fluid from cancer patients, and from extracted breast tumors, as described in co-pending U.S. patent application, Ser. No. 932,781. Briefly, milk was obtained from cancer-free donors using a breast pump. Samples were frozen within 5 to 10 minutes after collection. Effusion fluids from breast cancer patients were obtained from Virginia Mason Hospital, Seattle, Wash. Effusion fluids were stored frozen at −20° C. The mucins were purified using a modification fication of the procedure described by Creeth et al. *Biochem. J.*, 167:557–569 (1977). Whole milk and effusion fluids were thawed, and, guanidine HCl (United States BioChemical Corp., Cleveland, Ohio) was added to a final concentration of 6M and the mixture was stirred until clear. Cesium chloride gradient purification, affinity chromatography and SDS-PAGE were then performed on the milk and effusion fluids as described in co-pending U.S. patent application, Ser. No. 932,781.

Neuraminidase Treatment

For purified mucins, neuraminidase enzyme isolated from *Vibrio cholerae* (CALBIOCHEM Brand Biochemicals, La Jolla, Calif.), 10 inhibitory units per well (Linsley et al., *Cancer Res.* 46:5444–5450 (1986)) was dissolved in 50 mM sodium acetate buffer (0.15M NaCl, 50 mM sodium acetate, pH 5.5, 0.1% $CaCl_2$ and 0.1% $NaN_3$) pH 5.5 ("neuraminidase treatment buffer"). The presence of $NaN_3$ was found to be necessary to limit growth of microorganisms during the incubation at 37° C.; $NaN_3$ improved the reproducibility of the assays. Purified mucins were immobilized on plastic plates with poly-L-lysine as described by Dion et al., *Biotechniques*, (Sep., 1983) incorporated by reference herein. Digestion was carried out at 37° C. for 1.5 hours using an enzyme concentration varying from 0.002 to 1 milliUnits (mU) per well. Digestion was stopped by washing the plates after an incubation of approximately 16 hours by raising the pH from 7 to 8. The timing of digestion was previously determined by titrating increasing concentrations of neuraminidase up to 0.5 U/ml of buffer and observing binding of the antibodies W1 and ONC-M8 to the treated mucin antigen.

Binding

The antibodies W1, M8, L17, C6 and 1B2 were tested for binding to the neuraminidase treated antigen adhered to the plastic plates as described above. Bound antibodies were detected by an indirect ELISA in which horseradish peroxidase (HRP)-conjugated goat anti-mouse immunoglobulins (Cappel, Malvern, Pa.) were added to the plates. Bound HRP conjugates were quantitated by incubation with substrate, o-phenylenediamine, ("OPD"), (Genetic Systems Corp., Seattle, Wash.) for 5 to 60 minutes at 23° C. The reaction was then stopped by the addition of an equal volume of 1.3N $H_2SO_4$. Absorbance at 490 nm (OPD) was measured on a microwell plate reader (Genetic Systems Corp., supra). Values are reported in milliabsorbance units ($A_{490} \times 1000$) and represent the average of duplicate determinations which have been corrected for background absorbance in the absence of added monoclonal antibody. Duplicate determinations generally varied by less than 10%.

Results

Figure 3:
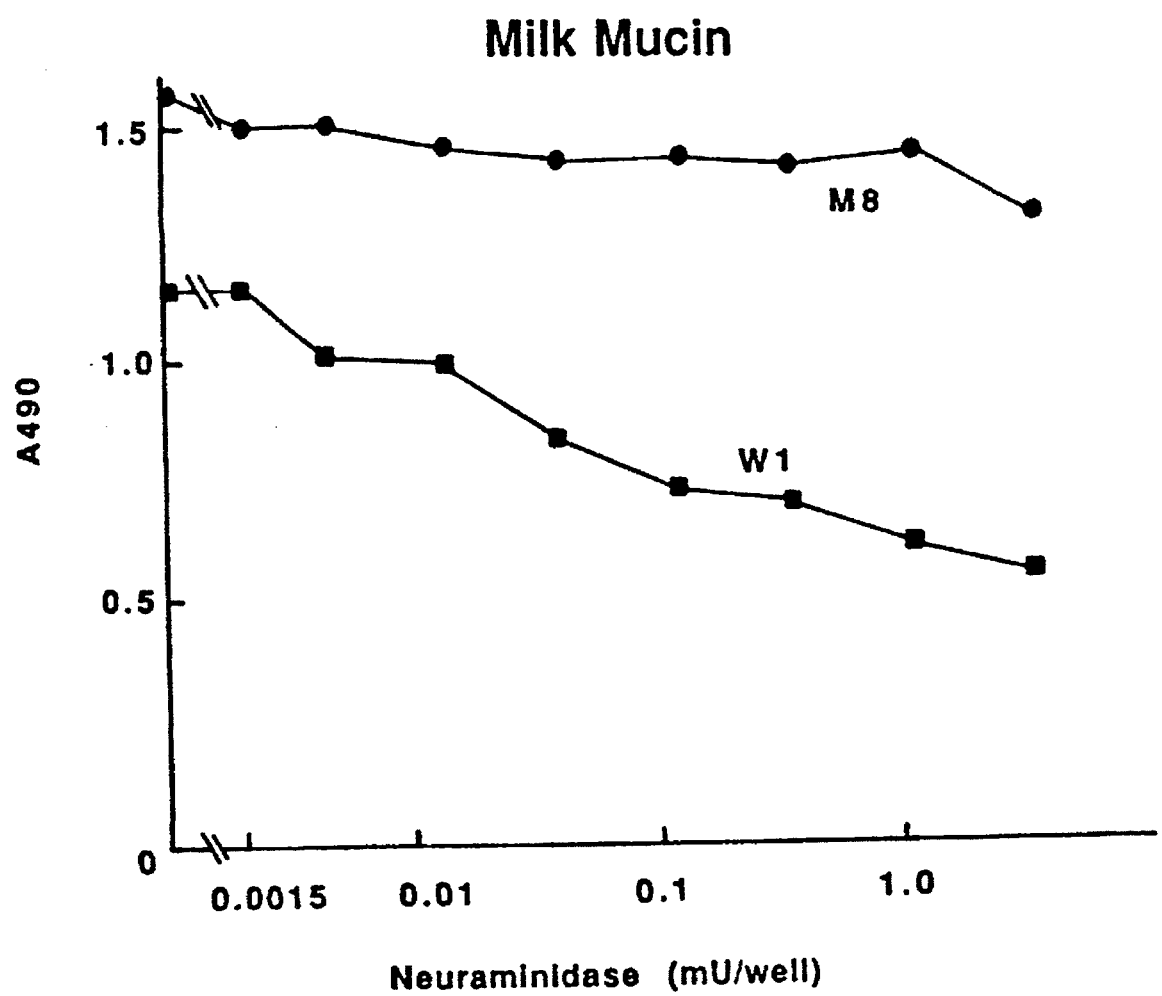
FIG. 3 is a graph depicting the binding of the ONC-M8 and W1 antibodies to purified milk mucin as a function of increasing neuraminidase concentration.
Figure 4:
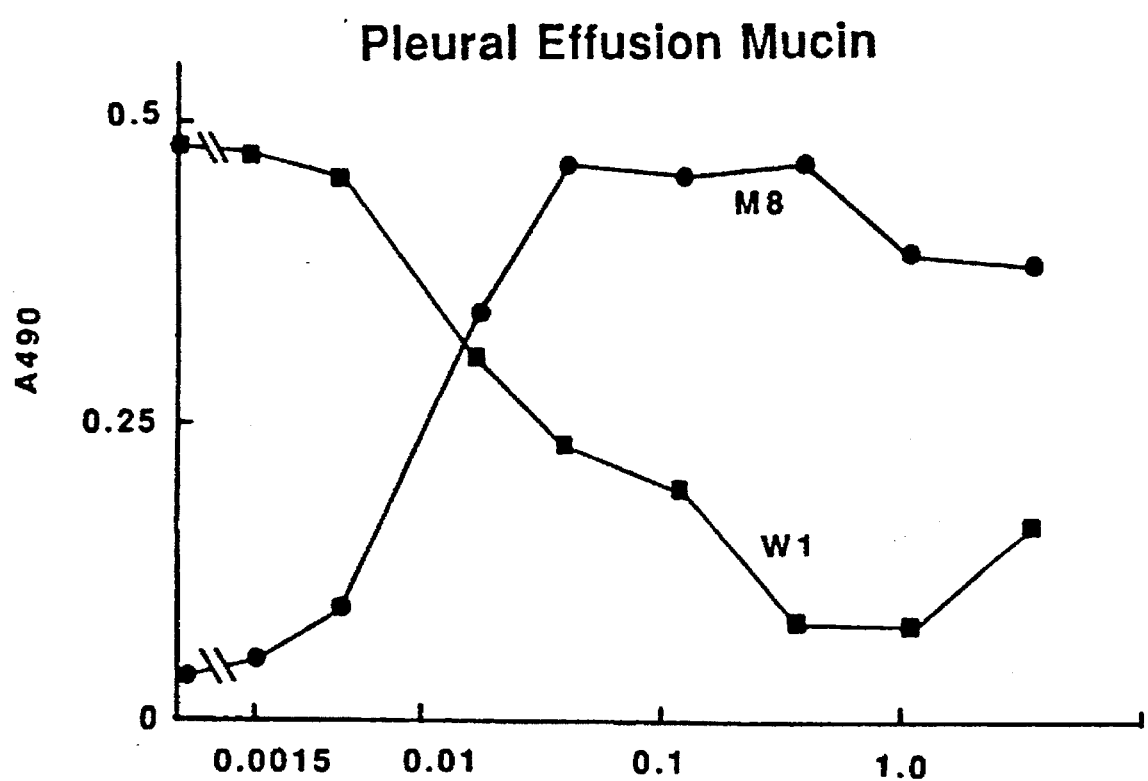
FIG. 4 is a graph of the binding of the ONC-M8 and W1 antibodies to pleural effusion mucin as neuraminidase concentration is increased.

As shown in FIG. 3 binding of the ONC-M8 antibody to purified, milk mucin was not appreciably altered by increasing concentrations of neuraminidase. Binding of the W1 antibody decreased with increasing concentrations of neuraminidase, as has been previously reported by Linsley et al, *Cancer Res.* 46:6380–6386 (1986). However, the ONC-M8 antibody exhibited increased binding to mucin purified from pleural effusions when samples were digested with increasing concentrations of neuraminidase (FIG. 4). These data indicate that the W1 epitope is neuraminidase sensitive resulting in decreased binding of W1 antibody, while the epitope recognized by the ONC-M8 antibody becomes exposed by neuraminidase treatment, resulting in increased binding of the ONC-M8 antibody. This result also suggests that tumor-associated mucins may be more highly sialylated than normal mucins.

The effects of neuraminidase treatment on binding of antibodies reactive with core and peripheral epitopes i.e. L17, C6 and 1B2 to purified pleural effusion mucin was examined following the procedures used to test binding of W1 and ONC-M8. The results are presented in Table 1.

TABLE I

Neuraminidase Treatment of Epitopes on Pleural Effusion Mucin

| ANTIBODY | ABSORBANCE$^{490}$ [1] | |
|---|---|---|
| | Without Treatment | With Treatment |
| W1 | 648 | 340 |
| M8 | 127 | 708 |
| L17 (Le$^x$) | 32 | 356 |

TABLE I-continued

Neuraminidase Treatment of Epitopes on
Pleural Effusion Mucin

| ANTIBODY | ABSORBANCE$^{490}$ [1] | |
|---|---|---|
|  | Without Treatment | With Treatment |
| C6 (I) | 80 | 766 |
| 1B2 (i) | 28 | 340 |

[1]Pleural effusion mucin was purified and treated as described above. Absorbance measurements were taken at 490 nm.

Binding of antibodies C6 and 1B2 which recognize branch-chain (C6) and linear (1B2) isomers of polylactosamine was enhanced by neuraminidase as shown in Table I. These components are backbone carbohydrate structures. Binding of both of these antibodies to pleural effusion mucin was enhanced by neuraminidase treatment, suggesting that binding of antibodies to core structures on mucins in sera from tumor patients might be enhanced by treatment to remove sialic acid.

The Le$^x$ epitope occurs in both sialylated and non-sialylated forms. The non-sialylated form is recognized by the L17 antibody (Hellstrom et al., *Cancer Res.* 46:3917–3923 (1986)). Binding of the L17 antibody was also enhanced after neuraminidase treatment. Antibodies which recognize non-sialylated peripheral structures may thus be used to detect epitopes which are normally masked by sialic acid, by treating with neuraminidase.

EXAMPLE III

A WGA capture assay was used for detection of antibodies capable of binding to mucins in human serum. This assay is described in co-pending U.S. patent application Ser. No. 932,781 filed Nov. 19, 1986 assigned to the same assignee as the present application, and incorporated by reference herein. Mucins in sera from normal patients and patients having various tumors (see Table II) were immobilized on 96 well, flat bottom, polystyrene microwell plates (Immulon II, Dynatech Laboratories, Inc., Alexandria, Va.) using *Tritium vulgaris* lectin (Wheat Germ agglutinin "WGA" from Sigma Chemical Co., St. Louis, Mo.). The microwell plates were prepared by the addition of 50 µl/well of a 20 µg/ml solution of WGA in 50 mM Tris-HCl containing 10 mM CaCl$_2$, and 10 mM MgCl$_2$ at pH 8.0. Following a two hour incubation at 25° C. to coat the plates with WGA, the solution was removed by aspiration. Serum samples from cancer patients or normal controls were diluted 1:50 in a buffer of 50 mM Tris-HCl at pH 8, containing 1 mM CaCl$_2$ and 1 mM MgCl$_2$ and added to the plates. The plates were then incubated for a period of from 1 to 4 hours at 25° C. and washed using buffer PBS and 2% fetal calf serum.

To conduct the assay, monoclonal antibodies L17 (ATCC No. HB8739), ONC-M8 and C6, were added at concentrations of 1 µg/ml.

Binding of the antibodies to the captured mucin in serum, was detected using OPD and measuring absorbance (A$_{490}$× 1000) as described above for the DDIA. Results are summarized in Table II.

TABLE II

WGA Serum Assay Without/With Neuraminidase Treatment

| Source[1] | L17 | | ONC-M8 | | C6 | |
|---|---|---|---|---|---|---|
|  | − | + | − | + | − | + |
| Prostate | 176 | 2800 | 2800 | 2800 | 153 | 2800 |
| Mesothelioma | 138 | 758 | 623 | 1311 | 147 | 2658 |
| Breast | 151 | 702 | 76 | 264 | 202 | 1406 |
| Breast | 82 | 2231 | 550 | 2096 | 97 | 2106 |
| Breast | 136 | 936 | 75 | 227 | 113 | 933 |
| Breast | 106 | 934 | 173 | 782 | 111 | 961 |
| Breast | 110 | 260 | 94 | 200 | 118 | 933 |
| Colon | 72 | 776 | 43 | 81 | 84 | 648 |
| SCLC[2] | 174 | 720 | 275 | 940 | 143 | 1291 |
| Lung | 114 | 2041 | 171 | 562 | 114 | 636 |
| Colon | 100 | 839 | 109 | 202 | 112 | 816 |
| Myeloma | 88 | 184 | 103 | 238 | 77 | 537 |
| Normal | 122 | 352 | 105 | 197 | 115 | 430 |
| Normal | 204 | 349 | 75 | 121 | 164 | 457 |
| Normal | 96 | 243 | 100 | 203 | 108 | 471 |

[1]Serum samples were taken from individuals having the tumor type indicated; normal samples were obtained from 3 separate individuals.
[2]SCLC is small cell lung carcinoma.

As can be seen from Table II, the amount of epitope detected after neuraminidase treatment dramatically increased for antibodies L17, ONC-M8 and C6. In addition, these antibodies demonstrated a much greater detection of tumor-associated epitope after neuraminidase treatment compared to the increase in detection of normal epitope after treatment with the enzyme. Antibody 1B2 was not tested in a serum assay. However, because binding of 1B2 to mucin was enhanced after neuraminidase treatment (Table I), it is likely that the sensitivity of a serum assay for the "i" epitope recognized by 1B2 would be similarly improved after neuraminidase treatment.

The present invention thus provides a method for treating ligands such as antigens, including ligands associated with disease or infection, to expose immunological binding sites which might otherwise remain unavailable for anti-ligand binding. Thus, binding sites which may be uniquely expressed on ligands associated with disease or infection, may be made available for binding to anti-ligands in immunoassays to detect the presence of diseases, such as cancer, in a human subject. In particular, a significant aspect of the present method of treating ligand is that the ligand may be directly treated in unpurified form, i.e. when present in a sample of body fluid such as whole blood sera, urine, sputum and effusion, to improve the detection of binding sites on the ligand.

While the present invention has been described in conjunction with preferred embodiments, one of ordinary skill, after reading the foregoing specification, will be able to effect various changes, substitutions of equivalents, and alterations to the compositions and methods set forth herein. It is therefore intended that the protection granted by the Letters Patent hereon be limited only by the appended claims and equivalents thereof.

The embodiments of the invention in which an exclusive property or privilege is claimed are defined as follows:

1. A method for determining the presence of a sialic acid masked tumor-associated antigenic determinant in an individual, comprising:

treating a serum sample obtained from the individual with neuraminidase;

contacting under conditions conducive to immune complex formation the neuraminidase treated serum sample with an antibody specific for the tumor-associated antigenic determinant; and detecting immune complex formation and thereby determining the presence of the sialic acid masked tumor-associated antigenic determinant in the individual.

2. The method of claim 1, wherein the tumor-associated antigenic determinant is on a mucin glycoprotein.

3. The method of claim 2, wherein the mucin glycoprotein is associated with breast tumors.

4. The method of claim 1, wherein the antibody is a monoclonal antibody.

5. The method of claim 4, wherein the monoclonal antibody is produced by a hybrid cell line designated ATCC No. HB 9209 or ATCC HB 8739.

6. The method of claim 1, wherein the antibody which specifically binds to the tumor-associated antigenic determinant is labeled to provide a detectable signal.

7. The method of claim 6, wherein the label is an enzyme, fluorophore, radionuclide or a second antibody which is labeled.

8. The method of claim 1, wherein the antibody specific for the tumor-associated antigenic determinant is adsorbed to a solid phase.

9. The method of claim 8, further comprising between the steps of contacting and detecting the step of separating unbound antibody from any immune complexes formed between the antibody and the tumor-associated antigenic determinant.

10. The method of claim 1, wherein the neuraminidase treated serum sample suspected of containing the tumor-associated antigenic determinant is immobilized to a solid phase prior to the step of contacting the sample with the antibody.

* * * * *